(12) United States Patent
Wang

(10) Patent No.: US 10,835,113 B2
(45) Date of Patent: Nov. 17, 2020

(54) METHOD AND APPARATUS FOR TRAVELLED DISTANCE MEASURING BY A CAPSULE CAMERA IN THE GASTROINTESTINAL TRACT

(71) Applicant: Capso Vision, Inc., Saratoga, CA (US)

(72) Inventor: Kang-Huai Wang, Saratoga, CA (US)

(73) Assignee: CapsoVision Inc., Saratoga, CA (US)

( * ) Notice: Subject to any disclaimer, the term of this patent is extended or adjusted under 35 U.S.C. 154(b) by 0 days.

(21) Appl. No.: 16/655,075

(22) Filed: Oct. 16, 2019

(65) Prior Publication Data

US 2020/0113422 A1 Apr. 16, 2020

Related U.S. Application Data

(62) Division of application No. 16/158,159, filed on Oct. 11, 2018, now Pat. No. 10,506,921.

(51) Int. Cl.
| | |
|---|---|
| *H04N 19/00* | (2014.01) |
| *A61B 1/04* | (2006.01) |
| *A61B 1/00* | (2006.01) |
| *H04N 19/139* | (2014.01) |
| *A61B 5/07* | (2006.01) |

(52) U.S. Cl.
CPC .......... *A61B 1/041* (2013.01); *A61B 1/00009* (2013.01); *A61B 5/073* (2013.01); *H04N 19/139* (2014.11)

(58) Field of Classification Search
CPC ..... A61B 1/041; A61B 1/00009; A61B 5/073; H04N 19/139
See application file for complete search history.

(56) References Cited

U.S. PATENT DOCUMENTS

| 7,983,458 B2 | 7/2011 | Wang et al. | |
|---|---|---|---|
| 9,936,151 B2 | 4/2018 | Wang et al. | |
| 2007/0098379 A1* | 5/2007 | Wang | A61B 5/14539 396/14 |
| 2009/0278921 A1* | 11/2009 | Wilson | H04N 5/2251 348/77 |
| 2014/0051924 A1* | 2/2014 | Wang | A61B 1/041 600/109 |
| 2015/0005643 A1* | 1/2015 | Whitman | A61B 17/02 600/476 |
| 2015/0016700 A1* | 1/2015 | Drozdzal | G06T 11/60 382/128 |

(Continued)

*Primary Examiner* — Zhihan Zhou
(74) *Attorney, Agent, or Firm* — Blairtech Solution LLC

(57) ABSTRACT

A method and system for determining a travelled distance by a capsule camera are disclosed. A current global motion vector for a current image in the image sequence is determined, where the current global motion vector corresponds to movement made by the capsule camera between the current image and a reference image associated with the image sequence. A travelled distance by the capsule camera in the GI tract is determined according to the current global motion vector and prior global motion vectors derived for prior images between an initial image and the current image, where the travelled distance is measured from an initial location associated with the initial image to a current location associated with the current image. A method and system for displaying an image sequence captured by a capsule camera are also disclosed. The travelled distances associated with the image sequence are displayed on a display.

5 Claims, 12 Drawing Sheets

(56) References Cited

U.S. PATENT DOCUMENTS

| | | | |
|---|---|---|---|
| 2015/0313445 A1* | 11/2015 | Davidson | A61B 1/31 600/109 |
| 2015/0320299 A1* | 11/2015 | Krupnik | A61B 1/00045 348/65 |
| 2015/0334276 A1* | 11/2015 | Ecker | H04N 5/341 348/76 |
| 2016/0037082 A1* | 2/2016 | Wang | G06T 5/006 348/65 |
| 2017/0109890 A1* | 4/2017 | Wang | G01B 11/2513 |

* cited by examiner

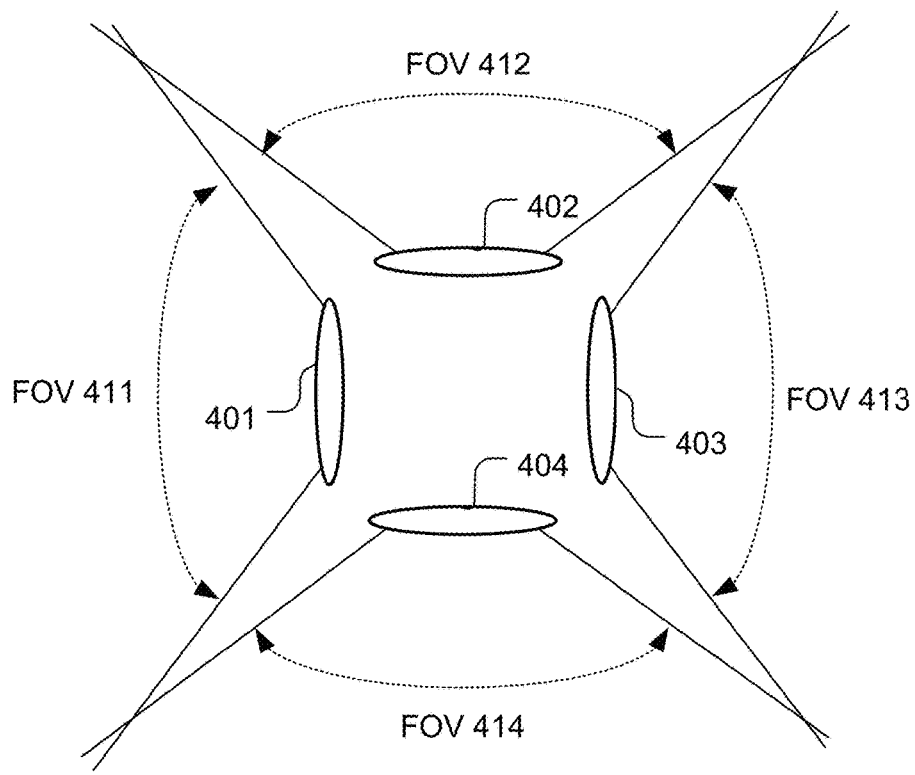
*Fig. 4*
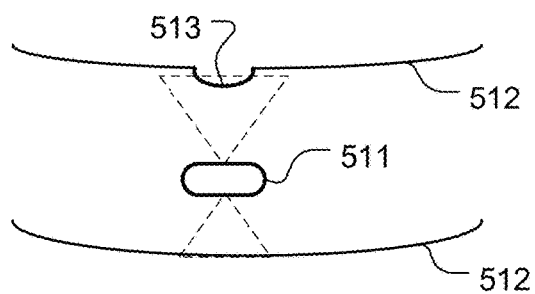 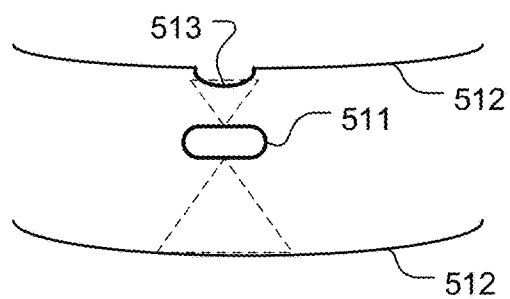
*Fig. 5A* *Fig. 5B*

METHOD AND APPARATUS FOR TRAVELLED DISTANCE MEASURING BY A CAPSULE CAMERA IN THE GASTROINTESTINAL TRACT

CROSS REFERENCE TO RELATED APPLICATIONS

The present invention is a Divisional Application of and claims priority to U.S. patent application Ser. No. 16/158,159, filed on Oct. 11, 2018, which is related to U.S. Pat. No. 9,936,151, issued on Apr. 3, 2018 and U.S. patent application Ser. No. 15/933,375, filed on Mar. 23, 2018. The U.S. Patent and U.S. Patent Application are hereby incorporated by reference in their entireties.

FIELD OF THE INVENTION

The present invention relates to estimating travelled distance by a capsule camera in the gastrointestinal (GI) tract based on images captured by the capsule camera when the capsule camera travelled through the GI tract.

BACKGROUND AND RELATED ART

Devices for imaging body cavities or passages in vivo are known in the art and include endoscopes and autonomous encapsulated cameras. Endoscopes are flexible or rigid tubes that pass into the body through an orifice or surgical opening, typically into the esophagus via the mouth or into the colon via the rectum. An image is formed at the distal end using a lens and transmitted to the proximal end, outside the body, either by a lens-relay system or by a coherent fiber-optic bundle. A conceptually similar instrument might record an image electronically at the distal end, for example using a CCD or CMOS array, and transfer the image data as an electrical signal to the proximal end through a cable. Endoscopes allow a physician control over the field of view and are well-accepted diagnostic tools. However, they do have a number of limitations, present risks to the patient, are invasive and uncomfortable for the patient, and their cost restricts their application as routine health-screening tools.

Because of the difficulty traversing a convoluted passage, endoscopes cannot easily reach the majority of the small intestine and special techniques and precautions, that add cost, are required to reach the entirety of the colon. Endoscopic risks include the possible perforation of the bodily organs traversed and complications arising from anesthesia. Moreover, a trade-off must be made between patient pain during the procedure and the health risks and post-procedural down time associated with anesthesia.

An alternative in vivo image sensor that addresses many of these problems is the capsule endoscope. A camera is housed in a swallowable capsule, along with a radio transmitter for transmitting data, primarily comprising images recorded by the digital camera, to a base-station receiver or transceiver and data recorder outside the body. The capsule may also include a radio receiver for receiving instructions or other data from a base-station transmitter. Instead of radio-frequency transmission, lower-frequency electromagnetic signals may be used. Power may be supplied inductively from an external inductor to an internal inductor within the capsule or from a battery within the capsule.

An autonomous capsule camera system with on-board data storage was disclosed in the U.S. Pat. No. 7,983,458, entitled "In Vivo Autonomous Camera with On-Board Data Storage or Digital Wireless Transmission in Regulatory Approved Band," granted on Jul. 19, 2011. This patent describes a capsule system using on-board storage such as semiconductor nonvolatile archival memory to store captured images. After the capsule passes from the body, it is retrieved. Capsule housing is opened and the images stored are transferred to a computer workstation for storage and analysis. For capsule images either received through wireless transmission or retrieved from on-board storage, the images will have to be displayed and examined by diagnostician to identify potential anomalies.

FIG. 1 illustrates an exemplary capsule system with on-board storage. The capsule system 110 includes illuminating system 12 and a camera that includes optical system 14 and image sensor 16. A semiconductor nonvolatile archival memory 20 may be provided to allow the images to be stored and later retrieved at a docking station outside the body, after the capsule is recovered. System 110 includes battery power supply 24 and an output port 26. Capsule system 110 may be propelled through the GI tract by peristalsis.

Illuminating system 12 may be implemented by LEDs. In FIG. 1, the LEDs are located adjacent to the camera's aperture, although other configurations are possible. The light source may also be provided, for example, behind the aperture. Other light sources, such as laser diodes, may also be used. Alternatively, white light sources or a combination of two or more narrow-wavelength-band sources may also be used. White LEDs are available that may include a blue LED or a violet LED, along with phosphorescent materials that are excited by the LED light to emit light at longer wavelengths. The portion of capsule housing 10 that allows light to pass through may be made from bio-compatible glass or polymer.

Optical system 14, which may include multiple refractive, diffractive, or reflective lens elements, provides an image of the lumen walls on image sensor 16. Image sensor 16 may be provided by charged-coupled devices (CCD) or complementary metal-oxide-semiconductor (CMOS) type devices that convert the received light intensities into corresponding electrical signals. Image sensor 16 may have a monochromatic response or include a color filter array such that a color image may be captured (e.g. using the RGB or CYM representations). The analog signals from image sensor 16 are preferably converted into digital form to allow processing in digital form. Such conversion may be accomplished using an analog-to-digital (A/D) converter, which may be provided inside the sensor (as in the current case), or in another portion inside capsule housing 10. The A/D unit may be provided between image sensor 16 and the rest of the system. LEDs in illuminating system 12 are synchronized with the operations of image sensor 16. Processing module 22 may be used to provide processing required for the system such as image processing and video compression. The processing module may also provide needed system control such as to control the LEDs during image capture operation. The processing module may also be responsible for other functions such as managing image capture and coordinating image retrieval.

After the capsule camera traveled through the GI tract and exits from the body, the capsule camera is retrieved and the images stored in the archival memory are read out through the output port. The received images are usually transferred to a base station for processing and for a diagnostician to examine. The accuracy as well as efficiency of diagnostics is most important. A diagnostician is expected to examine all images and correctly identify all anomalies. Furthermore, it is desirable to gather location information of the anomalies, which is useful for possible operations or treatment of the anomalies. While various location detection devices could be embedded or attached to the capsule device, it is desirable to develop methods for determining the travelled distance based on images captured.

BRIEF SUMMARY OF THE INVENTION

A method and system for determining a travelled distance by a capsule camera are disclosed. According to this method, an image sequence is received, where the image sequence is captured by the capsule camera when the capsule camera moves through a GI (gastrointestinal) tract. Distance information associated with object distances between the capsule camera and multiple points in a current image in the image sequence is received. The current image is normalized according to the object distances between the capsule camera and the multiple points in the current image to generate a normalized current image. A current global motion vector for a normalized current image in the image sequence is determined, where the current global motion vector corresponds to movement made by the capsule camera between the normalized current image and a normalized reference image associated with the image sequence. A travelled distance by the capsule camera in the GI tract is determined according to the current global motion vector and prior global motion vectors derived for prior images between a normalized initial image and the normalized current image, where the travelled distance is measured from an initial location associated with the normalized initial image to a current location associated with the normalized current image.

The travelled distance can be estimated by accumulating capsule movements in a longitudinal direction of the GI tract based on the current global motion vector and the prior global motion vectors. Furthermore, the capsule movement associated with a target global motion vector in the longitudinal direction of the GI tract can be determined by projecting the target global motion vector to the longitudinal direction. Images of the image sequence may comprise panoramic images, where each panoramic image corresponds to a scene in a field of view covering 360-degree of a section of GI tract wall around the capsule camera.

In one embodiment, a global motion vector is derived for a target image by dividing the target image into blocks for deriving individual motion vectors for the blocks and the global motion vector is derived from the individual motion vectors. In another embodiment, the global motion vector is derived for a target image by applying affine motion model between the target image and a target reference image.

The method may further comprise providing information associating the travelled distance with images from the image sequence. For example, the information associating the travelled distance with the images from the image sequence may comprise a current travelled distance and an identification of a corresponding image.

The travelled distance may be measured in the forward or backward direction. When measured in the forward direction, the current image is temporally after the initial image. When measured in the backward direction, the current image is temporally prior to the initial image.

A method and system for displaying an image sequence captured by a capsule camera are also disclosed. According to this method, an image sequence is received, where the image sequence is captured by the capsule camera when the capsule camera moves through a GI (gastrointestinal) tract. Travelled distances associated with the image sequence are presented on a display, where each travelled distance corresponds to an estimated distance measured from an initial location associated with an initial image in the image sequence to a current location associated with a current image in the image sequence. One or more graphic representations being representative of travelled distances are displayed on the display according to locations on said one or more graphic representations.

The above method may further comprise displaying an indicator on at least one of said one or more graphic representations to indicate a corresponding image associated with a target location pointed by the indicator. In addition, the method may comprise displaying the corresponding image associated with the target location pointed by the indicator on the display. The above method may further comprise displaying the corresponding image associated with the target location pointed by the indicator on the display.

In the above method, the current travelled distance can be accumulated from global motion vectors associated with the initial image to the current image in the image sequence. The global motion vectors are derived from normalized images of the image sequence and each normalized image is generated by normalizing a corresponding image according to distances between the capsule camera and multiple points in the corresponding image.

BRIEF DESCRIPTION OF THE DRAWINGS

FIG. 4 illustrates a simplified cross sectional view of a four lens sub-systems, where the optical axes are 90° apart in the objective space.

FIG. 5A and FIG. 5B illustrate two examples of camera-object distance in the GI tract environment, where in FIG. 5A, the camera is located further from the object (a polyp) on the GI wall than the example in FIG. 5B.

DETAILED DESCRIPTION OF THE INVENTION

Figure 1:
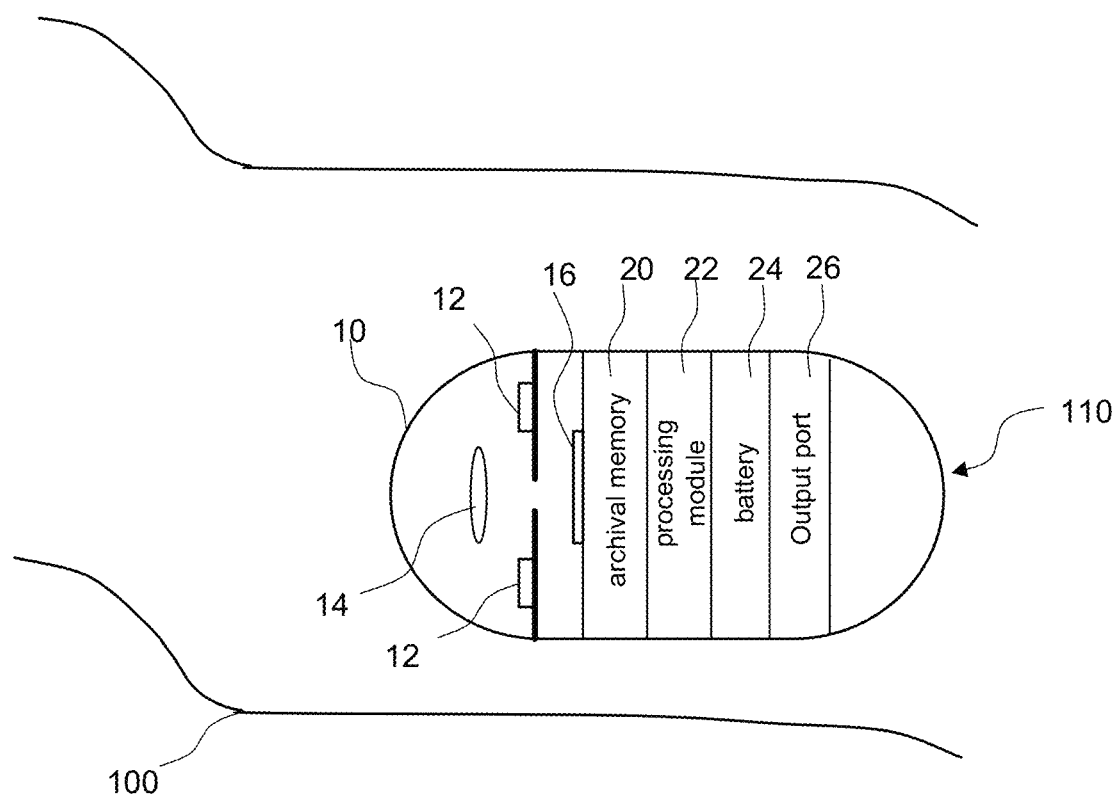
FIG. 1 illustrates an exemplary capsule system with on-board storage, where the capsule system includes illuminating system and a camera that includes optical system and image sensor.

It will be readily understood that the components of the present invention, as generally described and illustrated in the figures herein, may be arranged and designed in a wide variety of different configurations. Thus, the following more detailed description of the embodiments of the systems and methods of the present invention, as represented in the figures, is not intended to limit the scope of the invention, as claimed, but is merely representative of selected embodiments of the invention. References throughout this specification to "one embodiment," "an embodiment," or similar language mean that a particular feature, structure, or characteristic described in connection with the embodiment may be included in at least one embodiment of the present invention. Thus, appearances of the phrases "in one embodiment" or "in an embodiment" in various places throughout this specification are not necessarily all referring to the same embodiment.

Furthermore, the described features, structures, or characteristics may be combined in any suitable manner in one or more embodiments. One skilled in the relevant art will recognize, however, that the invention can be practiced without one or more of the specific details, or with other methods, components, etc. In other instances, well-known structures, or operations are not shown or described in detail to avoid obscuring aspects of the invention. The illustrated embodiments of the invention will be best understood by reference to the drawings, wherein like parts are designated by like numerals throughout. The following description is intended only by way of example, and simply illustrates certain selected embodiments of apparatus and methods that are consistent with the invention as claimed herein.

Endoscopes are normally inserted into the human body through a natural opening such as the mouth or anus. Therefore, endoscopes are preferred to be small sizes so as to be minimally invasive. As mentioned before, endoscopes can be used for diagnosis of human gastrointestinal (GI) tract. The captured image sequence can be viewed to identify any possible anomaly. If any anomaly is found, it is of interest to identify the characteristics of the anomaly as well as its location. Accordingly, the present invention discloses an endoscope incorporating a means for estimating travelled distance by the camera within the GI tract based on the captured images of the GI tract.

In the past, certain kinds of localization components, such as an accelerator, gyrator, etc., have been used to trace the ingestible device in the GI tract as the ingestible device containing these components passes through the GI tract. However, the subject usually does not remain stationary after swallowing the ingestible device. When the subject moves, these components cannot reliably differentiate the movement of torso or the device in the GI tract. What a component records is the combination of both movements. In order to develop reliable travelled distance estimation, the present invention discloses an image based approach. In particular, the present invention discloses travelled distance estimation based on global motion vectors derived from an image sequence captured when the capsule camera travelled through the GI tract. By using a global motion estimation method, the trace of the longitudinal direction is the trace of the device movement relative to the GI tract. Therefore, it records the GI tract longitudinal curve much more reliably. Although the bowel within the body is not completely fixed within the torso, however its uncertainty is much smaller than the entire torso movement.

Motion estimation is a technique that is widely used in video compression to estimate movement between images so as to compensate the motion and reduce the differences between images. With the reduced differences, the bitrate required to encode the video sequence becomes substantially reduced. The motions in a scene are usually described by a motion field or motion vectors. The motion may correspond to local motion associated with a moving object within the scene or global motion associated with a large area or a whole frame. The global motion is often caused by camera panning or camera motion. For example, in a video sequence captured by a camera on a moving vehicle facing in a direction perpendicular to the moving direction, motion vectors in the images will be predominantly uniform and the main motion vector corresponds to a global motion vector. If the camera optical parameters are known, the global motion vector (i.e., movement between two images) can be modelled by the movement of the camera.

Figure 2:
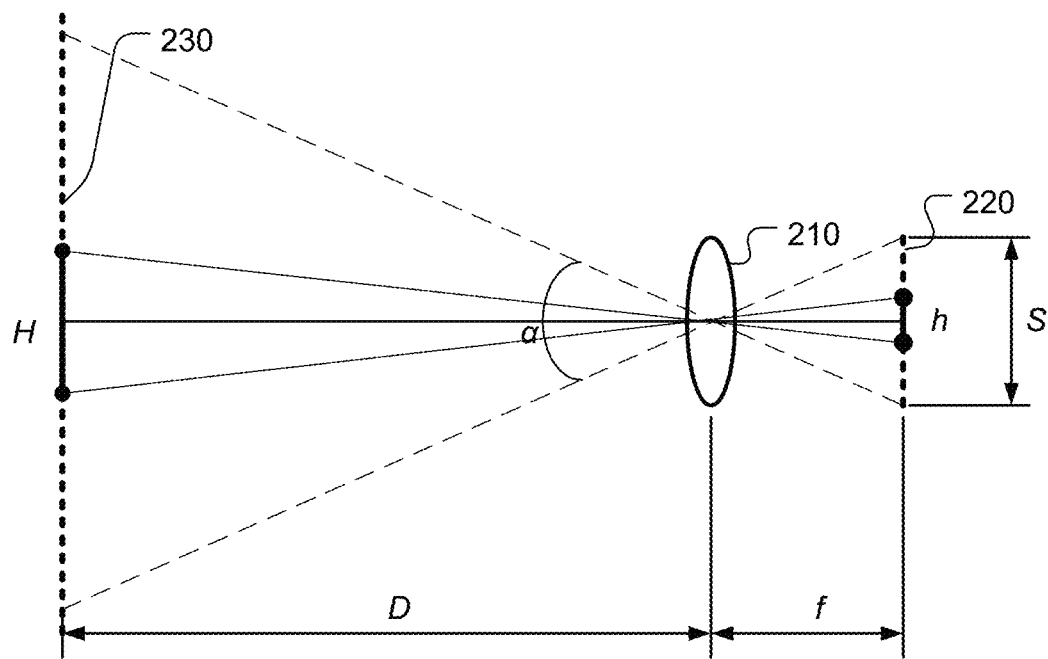
FIG. 2 illustrates a simplified example of camera geometry, where the image sensor is placed at the focal plane behind the lens.

FIG. 2 illustrates a simplified example of camera geometry. In a camera system, the image sensor is placed at the focal plane 220 behind the lens 210. The camera can capture a scene within the field of view extending an angle α. The focal length f is the distance between the lens and the image sensor. The focal length often is fixed for endoscopic applications and is known by design. If the distance D between the camera and an object is known, the dimension of an object can be determined from the captured image by measuring the size of the object image in the image. For example, if an object 230 with height H is at distance D from the camera, the object image height H can be derived from the object image height h in the image according to:

$$H = \frac{D}{f} h. \quad (1)$$

In the above equation, h is measured from the image, the focal length f is known by design, and the distance D is determined by a selected distance measuring means such as structured light technology. Accordingly, if the distance can be determined, the object dimensions can be derived. The object size in the image can be measured in physical dimension. However, the image is captured digitally and the size measurement may be more convenient in terms of the number of pixels. Since the physical dimension of image sensor surface and the optical footprint are known. Also, the number of pixels is known (e.g. 320×240). Therefore, the object image size in the image can be measured in a number of pixels and converted physical object image size in the image.

As shown above, the object image size in the image depends on the actual object size and its distance from the camera. A smaller object at a closer distance may appear to have the same size as a larger object in the image at a farther distance.

Figure 3:
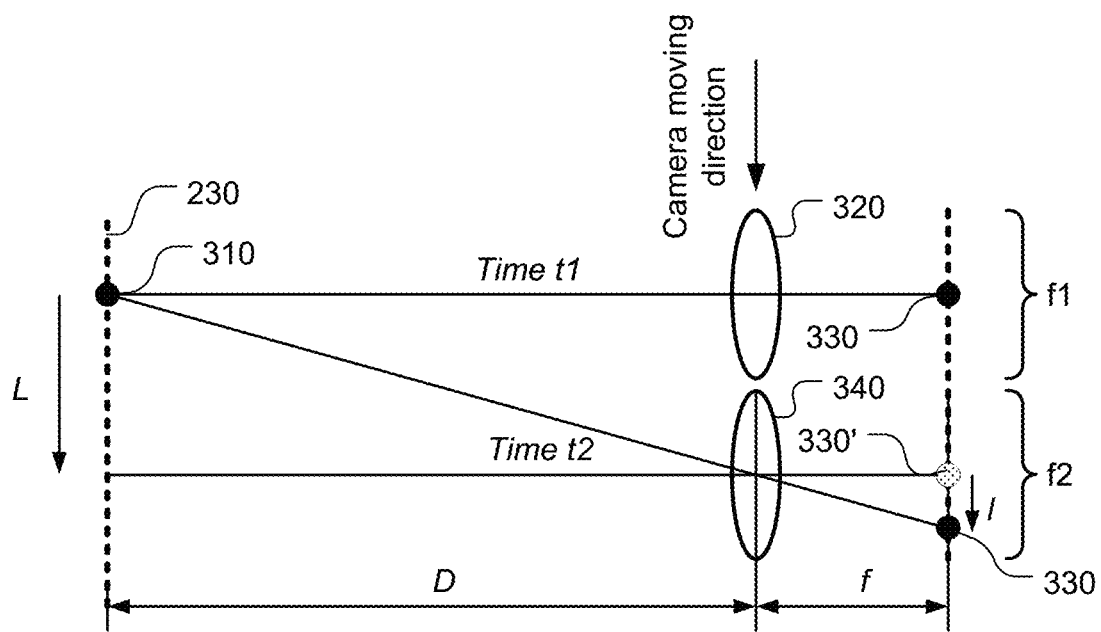
FIG. 3 illustrates a simplified example of travelled distance estimation based on the global motion vector and the camera optical parameters.

FIG. 3 illustrates a simplified example of travelled distance estimation based on the global motion vector and the camera optical parameters. In this example, object 310 is stationary and the camera is moving. At time t1, the camera is at location 320 and the object 310 is in front of the camera. The object 310 is projected to the center location 330 of captured frame f1. At time t2, the camera is moved to location 340. Object 310 is projected to image location 330 of captured frame f2. In captured frame f2, the object location (330') corresponding to the object location (330) in captured frame f1 is indicated. The motion vector between object location 330 and object location 330' can be derived from captured frame f1 and captured frame f2 using motion estimation techniques. In particular, the motion vector corresponds to a global motion vector ($MV_g$) can be derived based on the images, where the motion vector is measured in number of pixels.

Since the image sensor size and resolution are also known, the actual length (l) of the motion vector can be determined according to l=|MV|×pl, where |MV| corresponds to the magnitude of the motion vector and pl corresponds to distance between pixels. The actual travelled distance L can be measured according to:

$$L = \frac{D}{f} l = \frac{D}{f} |MV| \times pl. \quad (2)$$

The concept of motion estimation can be applied to images captured by a capsule camera while traveling through the GI tract of a human subject. However, the motion vectors derived from the images of the GI tract captured by a capsule camera are far from the idealistic motion vectors illustrated in FIG. 3 as described above. The capsule camera may correspond to a forward-looking camera located at one end of an elongated capsule device. A global motion vector representing the camera movement may not be derived easily. The capsule camera may also correspond to a panoramic-view camera, such as the capsule camera system described in U.S. Pat. No. 7,940,973, issued on May 10, 2011. FIG. 4 illustrates a simplified cross sectional view of a four lens sub-systems 401-404, where the optical axes are 90° apart in the objective space. Lens sub-system 401 covers a field of view 411, lens sub-system 402 covers a field of view 412, lens sub-system 403 covers a field of view 413, and lens sub-system 404 covers a field of view 414. The sub-images captured by the multiple cameras can be joined together to form a 360° wide-angle image.

When the capsule camera travels through the GI tract, the capsule camera may not the positioned in the center of the GI tract. Therefore, the distances from the camera to the GI wall may not be the same. FIG. 5A and FIG. 5B illustrate two examples of camera-object distance in the GI tract environment. In FIG. 5A, camera 511 is located further from object 513 (a polyp) on the GI wall 512 than the example in FIG. 5B. Therefore, the object in the image corresponding to the case of FIG. 5A will appear to be smaller than the object in the image corresponding to the case of FIG. 5B.

Figure 6A:
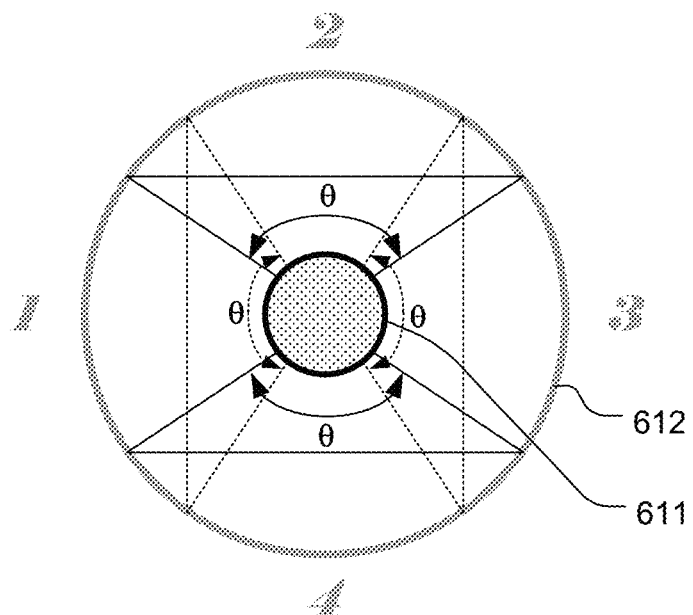
FIG. 6A illustrates a cross section of the GI tract for a scenario that capsule camera is located in the center of GI tract wall, where the GI tract wall is modelled as a perfect round tube.
Figure 6B:
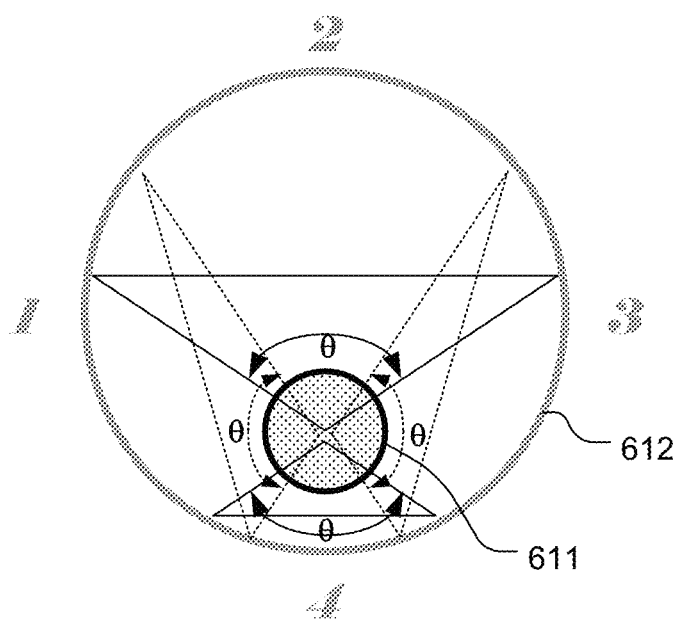
FIG. 6B illustrates another scenario where the capsule is closer to the bottom side of the GI wall.

FIG. 6A illustrates a cross section for a scenario that capsule camera 611 is located in the center of GI tract wall 612. In FIG. 6A, the GI tract wall is modelled as a perfect round tube. Each of the panoramic cameras covers a Field of View (FOV) corresponding to θ. As shown in FIG. 6A, the FOV of neighboring cameras is slightly overlapped. The overlapped image areas will be processed to form seamless images. Since the capsule is in the center of the GI tract, objects on the GI wall having the same size should appear to have the same size in front of respective cameras. FIG. 6B illustrates another scenario where the capsule is closer to the bottom side of the GI wall. In this case, for objects on the GI wall having the same size, the object in image 4 (i.e., the image captured by the camera looking downward) will appear much larger than the object in picture 2 (i.e., the image captured by the camera looking upward). On the other hand, the object in images 1 and 3 will appear to be smaller than the object in image 4, but larger than the object in image 2.

Figure 7A:
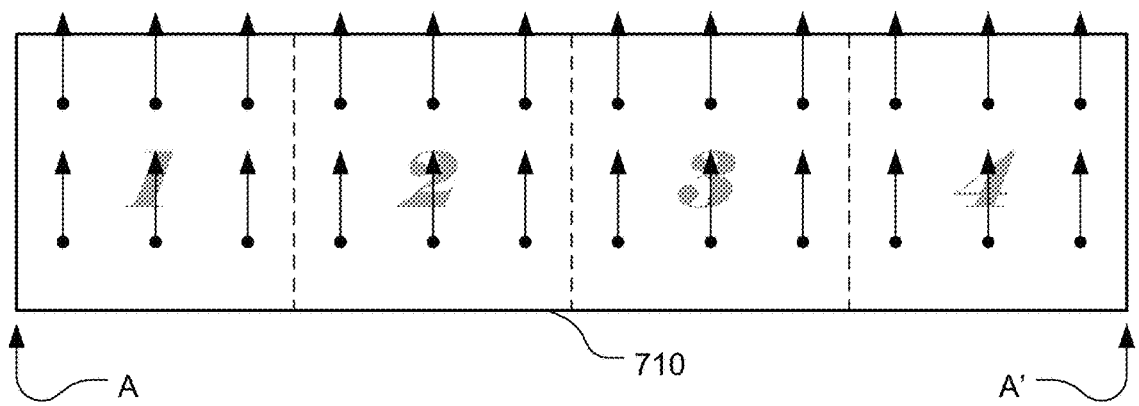
FIG. 7A illustrates a uniform motion vector field in the image captured by the panoramic camera in the scenario of FIG. 6A.
Figure 7B:
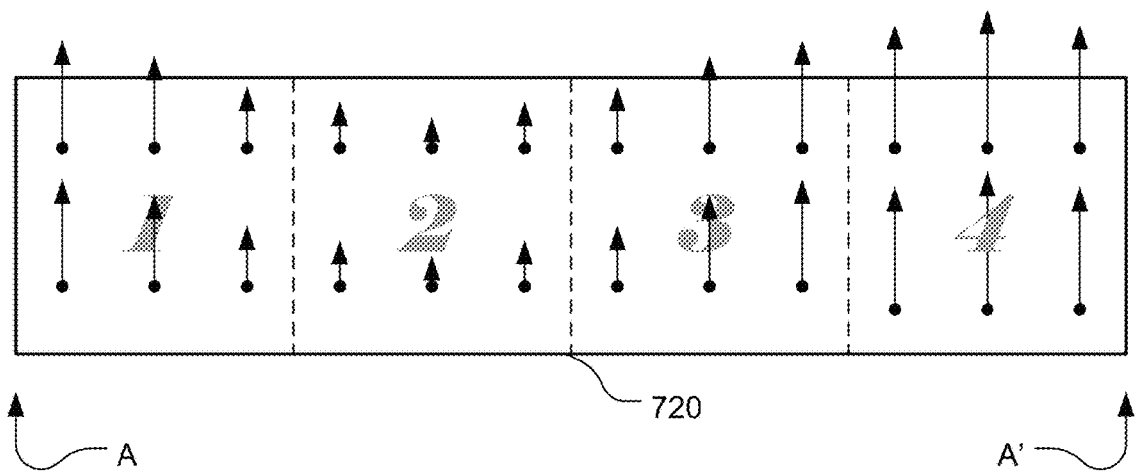
FIG. 7B illustrates a varying motion vector field in the image captured by the panoramic camera in the scenario of FIG. 6B.

In the case of FIG. 6A, if the capsule device travels in the longitudinal direction of the GI tract, the image 710 captured by the panoramic camera will show a uniform motion vector field as illustrated in FIG. 7A. In FIG. 7A, panoramic image 710 consists of 4 sub-images as numbered with the seamless sub-image boundary indicated by a dash line. Since the panoramic camera in this example covers a 360° view, the right edge (A') of panoramic image 710 is wrapped around to the left edge (A). In the case of FIG. 6B, if the capsule device travels in the longitudinal direction of the GI tract, the images 720 captured by the panoramic cameras will show a varying motion vector field depending on the horizontal location of the image as illustrated in FIG. 7B. For sub-image 4, the camera is very close to the GI tract wall and the object will look much larger than the image that would be captured by camera on the opposite side (i.e., associated with sub-image 2). Accordingly, the motion vector in sub-image 4 will be much larger than the motion vector in sub-image 2. According to conventional motion estimation techniques, the global motion won't be recognized.

In the scenario illustrated in FIG. 7B, the varying motion vectors are caused by different distance between a respective camera and the GI tract wall. The optical parameters of the cameras are known by design. Therefore, if the distance between a respective camera and the GI tract wall is also known, each motion vector can be used to estimate the travelled distance by the camera according to equation (2) as illustrated in FIG. 3. The travelled distance by the capsule device can be derived as the average of individual travelled distances estimated based on individual motion vectors. In another embodiment, the motion vectors can be normalized based on the distance between a respective camera and the GI tract wall. For example, the motion vectors may be normalized with respect to a nominal distance, such as the average distance between a respective camera and the GI tract wall (i.e., the distance between a respective camera and the GI tract wall in FIG. 6A). In FIG. 7B, while the magnitude of motion vectors varies along the horizontal direction, these motion vectors should be mapped to the same travelled distance by the capsule camera. In other words, for two motion vectors, MV1 and MV2 for two different image blocks having distances D1 and D2 respectively between the respective camera and the GI tract wall, the following equation holds:

$$L = \frac{D1}{f}|MV1| \cdot pl = \frac{D2}{f}|MV2| \cdot pl. \tag{3}$$

Therefore, the two motion vectors are related according to D1·|MV1|=D2·|MV2|. If all motion vectors are normalized with respect to a nominal distance $\overline{D}$, the normalized motion vectors, MV1' and MV2' with respect to $\overline{D}$ (i.e., the corresponding motion vector with distance $\overline{D}$) are derived as:

$$|MV1'| = \frac{D1}{\overline{D}}|MV1|, \text{ and} \tag{4}$$

$$|MV2'| = \frac{D2^-}{\overline{D}}|MV2|. \tag{5}$$

Figure 8:
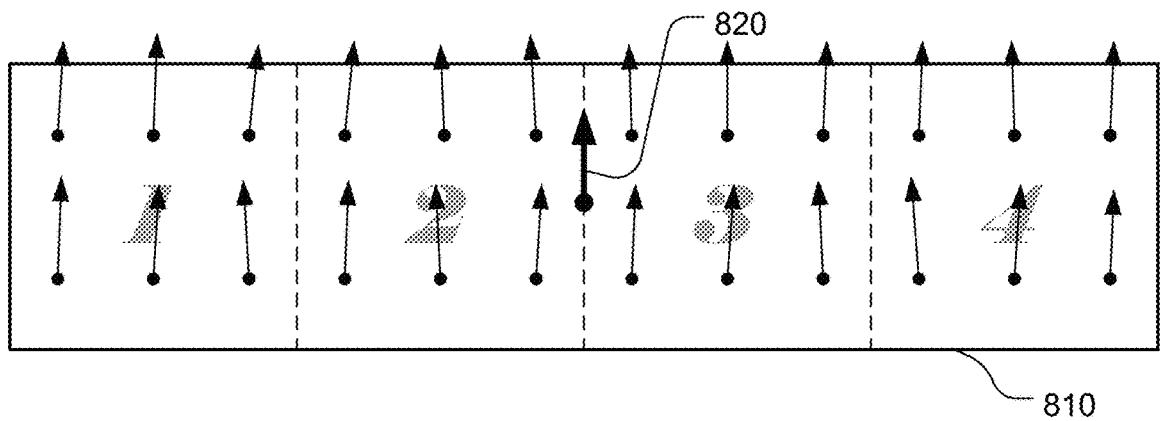
FIG. 8 illustrates an example of normalized motion vectors according to the distance between respective camera and the GI tract wall.

FIG. 8 illustrates an example of normalized motion vectors according to the distance between respective camera and the GI tract wall. Due to noise in the image, motion vectors derived from the panoramic image 810 may not be accurate. Accordingly, the normalized motion vectors may not be accurate either. However, the average normalized motion vector (820) will provide a more reliable estimation of the true global motion. In FIG. 8, the normalized motion vectors are normalized with respect to the average distance between the cameras and the GI tract walls. While the average of normalized motion vectors can be used to estimate the global motion vector, other techniques may also be used to estimate the global motion vector. For example, the median or the dominant motion vector can be used to estimate the global motion vector.

In the above discussion, simplified GI tract wall model (i.e., a cylindrical tube) is used to illustrate that the varying motion vectors may be a result of different distance between the GI tract wall and the capsule camera. Under a realistic environment, the situation may be much complicated. For example, the GI tract wall is far from the simplified cylindrical tube model and the distance between the capsule camera and the GI tract wall varies from location to location. Furthermore, the longitudinal axis of the capsule camera may not be aligned with the longitudinal direction of a section of the GI tract where the capsule camera is located. In addition, the capsule camera may undergo 3D movement such as tilting and rotating, which makes the motion estimation process much more complicated.

The longitudinal direction can be derived from the motion vectors. For example, the motion vectors can be smoothed and the smoothed motion vectors represent the shape of the trace of the GI tract inside the torso. The information regarding the longitudinal distance travelled by the capsule camera may give the doctor a good locational information for surgery for a lesion found in the images.

Figure 9:
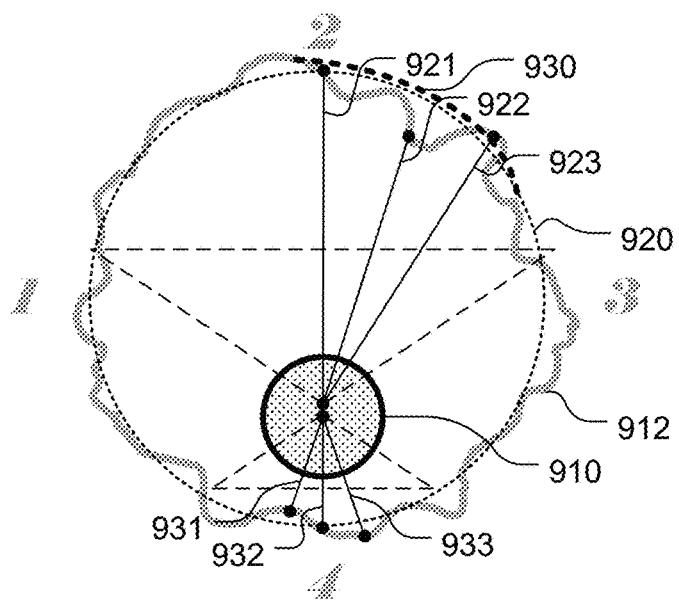
FIG. 9 illustrates a scenario of varying distance between the capsule camera and the GI tract wall due to the non-smooth GI tract wall as well as the non-center location the capsule camera.

FIG. 9 illustrates a scenario of varying distance between the capsule camera and the GI tract wall due to the non-smooth GI tract wall 912 as well as the non-center location the capsule camera 910. Distance lines 921, 922, 923, 931, 932 and 933 illustrate varying distances due to the non-smooth GI tract wall 912 as well as the non-center location and tilting of the capsule camera 910. While the GI tract walls are non-smooth, each cross section of the GI tract wall may be modelled as a circle 920 as shown in FIG. 9. The non-smooth surface of the GI tract will cause local distortion in the image captured by the capsule camera. For example, a dot having a distance line 922 will appear large in the image than the dot having a distance line 921 or 923 since the dot having a distance line 922 is closer to the camera than the other two dots.

The non-smooth surface of the GI tract wall will cause inaccuracy for the motion estimation process. There are various motion estimation methods known in the field of video compression. Among them, block matching has been a very popular search algorithm, where the block matching process searches for a best match block in a reference picture (i.e., a previously processed picture) for a given block in a current picture. A motion vector is used to specify the movement between the two corresponding block. The motion may correspond to a simple translational movement that represents a block movement by shifting the block horizontally and/or vertically by an offset. The motion may correspond to a more complicated movement that involves two-dimensional block rotations as well as two-dimensional deformations. The affine model is capable of describing two-dimensional block rotations as well as two-dimensional deformations to transform a square (or rectangles) into a parallelogram. This model can be described as follows:

$$x'=a0+a1*x+a2*y, \text{ and}$$

$$y'=b0+b1*x+b2*y.$$

In the above equations, (x, y) corresponds to the pixel coordinates of the current image and (x'y') corresponds to the pixel coordinates of the reference image. For each pixel A(x, y) in the current image, the motion vector between this pixel and its corresponding reference pixel A'(x', y') is (a0+a1*x+a2*y, b0+b1*x+b2*y). Therefore, the motion vector for each pixel is also location dependent. The affine motion estimation is also well known in the art and the details will not be repeated herein.

Figure 10:
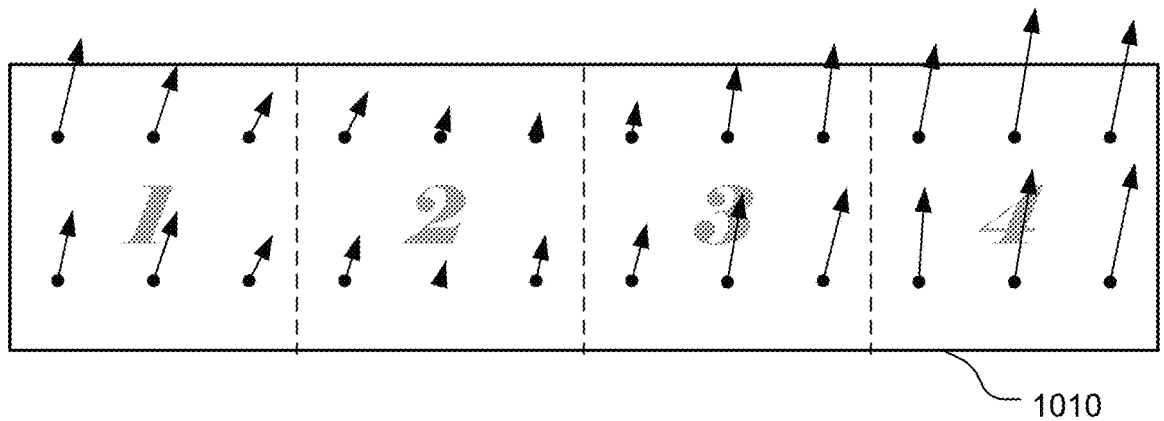
FIG. 10 illustrates an example of motion vector field for the scenario in FIG. 9.

As mentioned above, the non-smooth surface of the GI tract wall will result in different distances between object locations corresponding to pixels in an image area and the camera. The local distance variation will cause negative impact on the accuracy of motion estimation result. Therefore, according to an embodiment of the present invention, the local variations in object-camera distances of pixels within a search area for motion estimation and the object-camera distances of pixels within a current block are normalized before performing the block matching process. For example, for a search area as indicated by an arc 930 in the cross section, the object-camera distances for pixels within the search area are normalized according to the object-camera distances of individual pixels. The object-camera distance normalization will enlarge a patch at a longer distance and shrink a patch in a closer distance. The image normalization based on object-camera distance can be performed on a sub-block basis by dividing the area into sub-blocks (e.g. 4×4 pixels) and each sub-block is associated with an individual object-camera distance. If the distance for a given sub-block is smaller than a nominal distance, the sub-block is shrunk proportionally according to the nominal distance-individual distance ratio. If the distance for a given sub-block is larger than a nominal distance, the sub-block is enlarged proportionally according to the nominal distance-individual distance ratio. As is known in image processing, pixel interpolation will be required during image enlargement or shrinking (i.e., scaling). After image normalization based on the object-camera distance, the motion estimation process should result in more accurate motion estimation results. The image normalization is mainly focused on the distance variations due to non-smooth surface of the GI tract walls. This normalization is used in the stage prior to motion estimation process so as to improve the accuracy of the motion estimation. Accordingly, the above image normalization to compensate the non-smooth surface of the GI tract wall is referred as local image normalization for object-camera distance variation. In one embodiment, the effect of distance variation due to the off-center location of the capsule camera will be treated after the motion vectors are derived. FIG. 10 illustrates an example of motion vector field for the scenario in FIG. 9 by taking into account of local image normalization to take care of varying object-camera distance. Without the local image normalization to compensate the effect of the non-smooth GI tract wall, the motion vectors derived would be less accurate.

Figure 11:
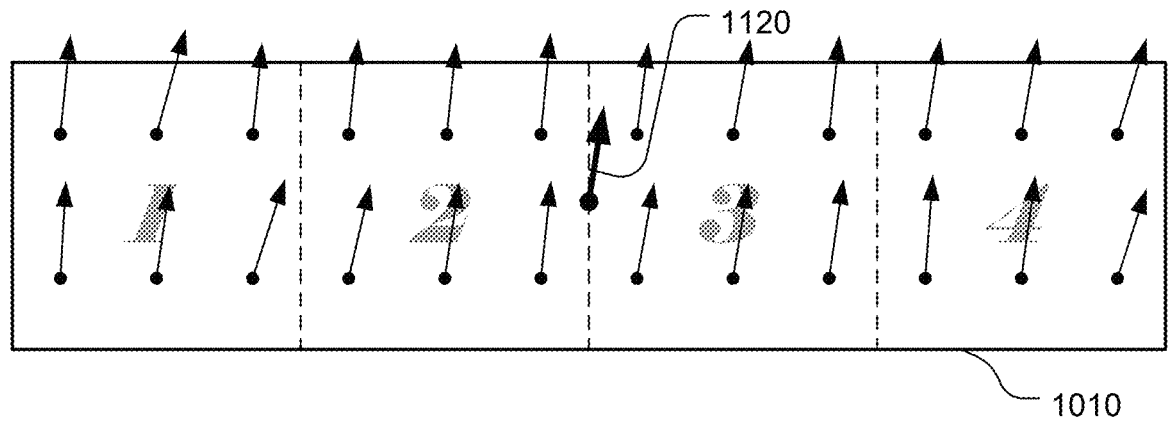
FIG. 11 illustrates an example of normalized motion vectors for the motion vectors in FIG. 10 by taking into account of local image normalization to take care of varying object-camera distance.

In FIG. 10, the motion vectors are mostly pointed toward up-right, which represents that case that the capsule device also rotates around its longitudinal axis. Furthermore, since the capsule device is off the center of the GI tract walls, the motion vectors in sub-image 2 are generally smaller than the motion vectors in sub-image 4. Therefore, the motion vector normalization illustrated in FIG. 7 and equations (4) and (5) can be applied to normalize the motion vectors in FIG. 10. In particular, the motion vector can be normalized with respect to a target distance, such as the average distance between the camera and the GI tract walls. FIG. 11 illustrates an example of normalized motion vectors for the motion vectors in FIG. 10. The average of normalized vectors (1120) can be used as the global motion vector for the capsule device.

Alternatively, the varying camera-GI tract wall in FIG. 9 could be normalized to a unit radius based on measured distance within the FOV, similar to the scenario shown in FIG. 6A. For example unit radius can be set to 1 cm or 1.25 cm.

Figure 12:
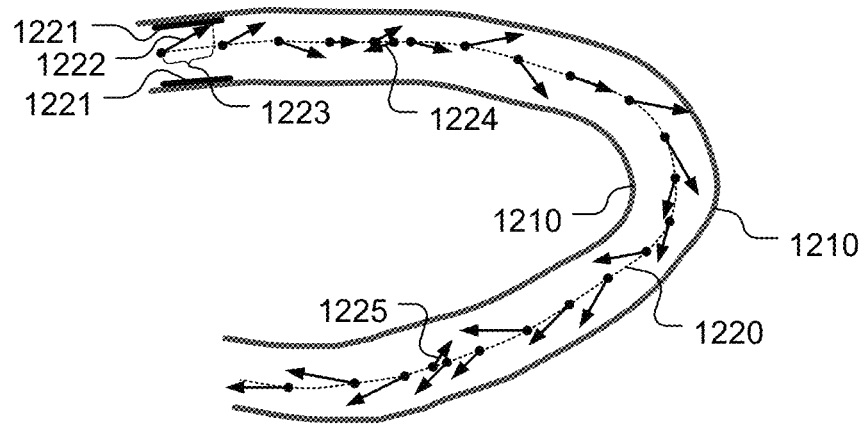
FIG. 12 illustrates an example of a section of the GI tract with a longitudinal direction in the center of the GI tract indicated by a dash line.

One intended usage of the global motion vector is to estimate the travelled distance by the capsule device inside the GI tract. The GI tract is folded within human body. From the point of view of the travelled distance by the capsule device, the capsule device movement in the longitudinal direction of the GI tract is of interest. Therefore, the movement in the longitudinal direction of the GI tract should be measured. In FIG. 12, a section of the GI tract 1210 is shown and a longitudinal direction in the center of the GI tract is indicated by a dash line 1220. An image area 1221 associated with the surface of a section of the GI tract is indicated by a thick line on the inner surface of the GI tract wall. A global motion vector 1222 may be derived based on the image area 1221. The image area 1221 may correspond to the 360° image of the target section. However, the image area 1221 may correspond to the partial image of the target section. The global motion vector may be determined by dividing the image area 1221 into blocks and individual motion vectors are derived first. A global motion vector is then derived from the motion vectors. However, the global motion vector may also be derived directly from the image area. For example, the parameters associated with a global motion vector (e.g. parameters for affine motion model) may be derived using the image area without dividing it into blocks.

Since the capsule device is moved in the GI tract under the action of peristalsis, it may not move accurately along the longitudinal direction. For example, the global motion vectors derived for various sections of the GI tract are shown by the arrows. In order to measure the travelled distance by the capsule device, the motion vector component in the longitudinal direction has to be determined. The motion vector component in the longitudinal direction can be determined by projecting the motion vector to the longitudinal direction. For example, motion vector 1222 is projected to the longitudinal direction to obtain the travelled distance 1223 associated with the motion vector 1222. The individual travelled distances derived from an image sequence for the GI tract can be accumulated to obtain the total travelled distance.

As is known in the field, the GI tract peristalsis may cause the capsule device to occasionally move backward (i.e., "retrograde") or oscillate. Therefore, the motion vector may occasionally point backward (e.g. motion vectors 1224 and 1225 in FIG. 12). When the capsule device moves backward, the associated motion vector contributes a negative value to the accumulated travelled distance.

Figure 13A:
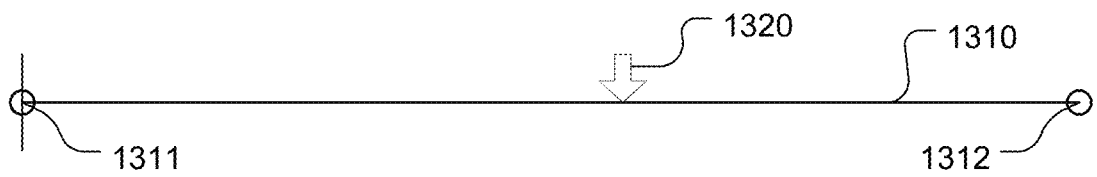
FIG. 13A-E illustrate various embodiments of displaying travelled distance information on a display.
Figure 13B:
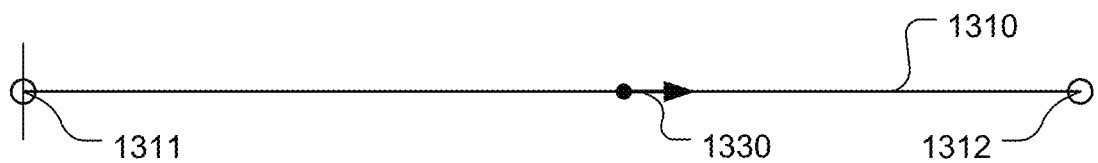
Figure 13C:
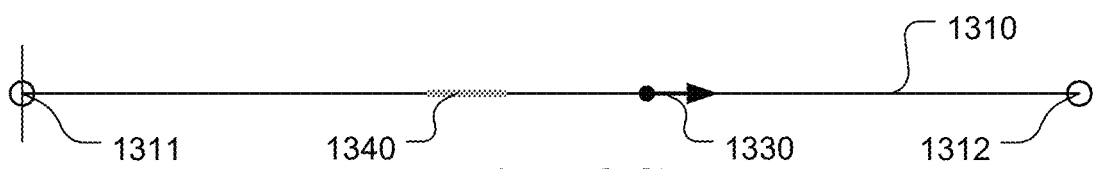

The results of estimated travelled distance can be present to a user (e.g. a physician) to evaluate the medical images collected by the capsule device while travelling through the GI tract. For example, the travelled distance in the longitudinal direction may be displayed as a horizontal line, where a reference point may be set as the origin. The horizontal distance corresponds to a travelled distance from the origin. For example, line 1310 in FIG. 13A corresponds to an example of displaying accumulated travelled distance, where the origin 1311 corresponds to first reference location and the ending point corresponds to a second reference location. The first reference location and the second reference location may correspond to particular anatomic parts of the GI tract. For example, the first reference location may correspond to the duodenum and the second reference location may correspond to the anus. The image being viewed may be displayed in another display window on a display device. The location on the longitudinal axis of the GI tract for the current image may be indicated on the horizontal longitudinal line 1310 by a marker, such as a downward arrow 1320. The particular anatomic part may be determined from the capture images according to the characteristics of these particular anatomic parts. The horizontal axis may be labelled according to the measured travelled distance. For example, the total length from the origin corresponding to the duodenum to the ending location corresponding to the anus may be 7.5 meters. The horizontal axis may be marked every 10 centimeters. Finer or coarser markers may also be used. In another embodiment, the global motion vector associated with the current image may be display as an arrow 1330 in FIG. 13B, where the arrow may point to forward direct or backward direction (i.e., retrograde movement). Furthermore, the location(s) for the retrograde movement may be indicated on the travelled distance line 1310. For example, a line segment 1340 corresponding to the distance of the retrograde movement may be overlaid on the travelled distance line 1310 as shown in FIG. 13C. Alternatively, the retrograde movement can be more explicitly represented by a backward transition 1352 from an original travelled distance line 1350a to another original travelled distance line 1350b as shown in FIG. 13D.

Figure 13D:
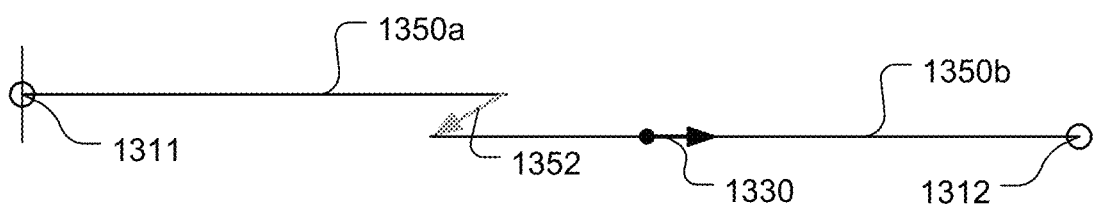
Figure 13E:
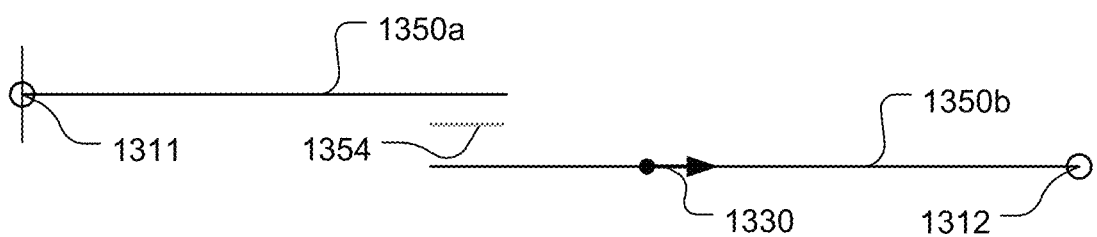

In FIG. 13E, a different display style is illustrated, where the transition 1352 of FIG. 13D is replaced by a line segment 1354 corresponding to the travelled distance associated with the retrograde movement. While one or more horizontal lines are used to represent the travelled distance, other graphic representations may also be used. For example, one or more horizontal bars may be used. In another example, a numerical number may be displayed to indicate the travelled distance and up/down arrows may be used to allow a user to select a desired travelled distance. The user may use an input device such as a computer mouse or buttons to control the selection.

Figure 14:
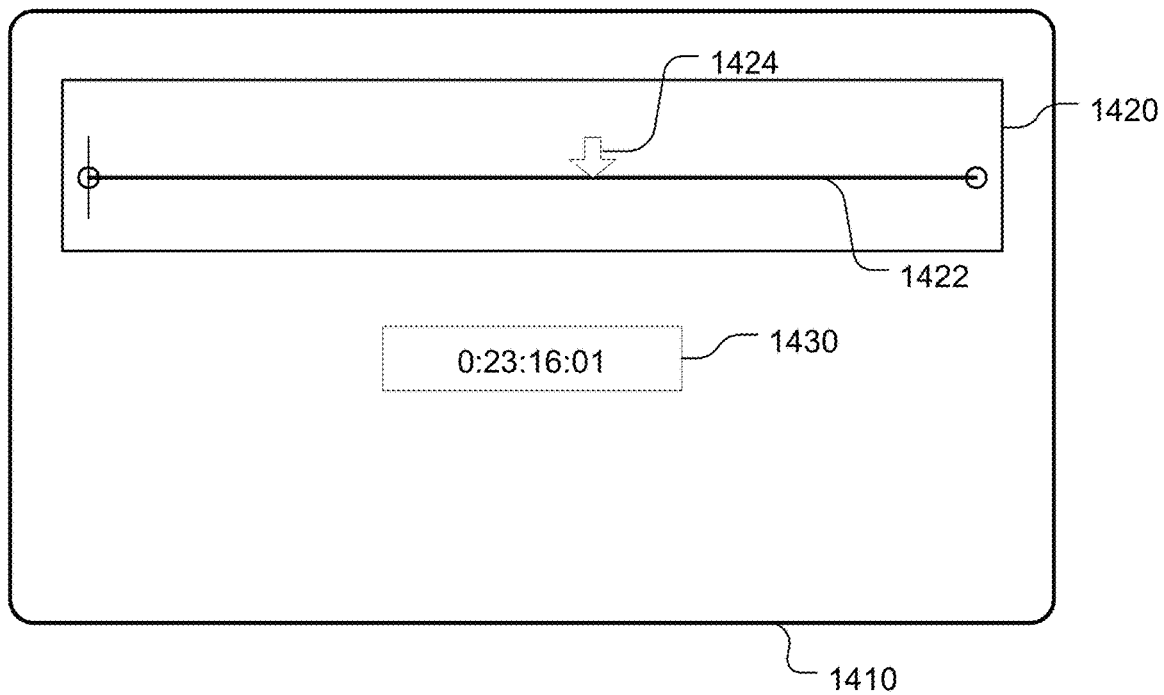
FIG. 14 illustrates an example of displaying the travelled distance information along with the image information, where a graphic representation of the travelled distance and the time code of the image as indicated by a marker is shown in area on a display.
Figure 15:
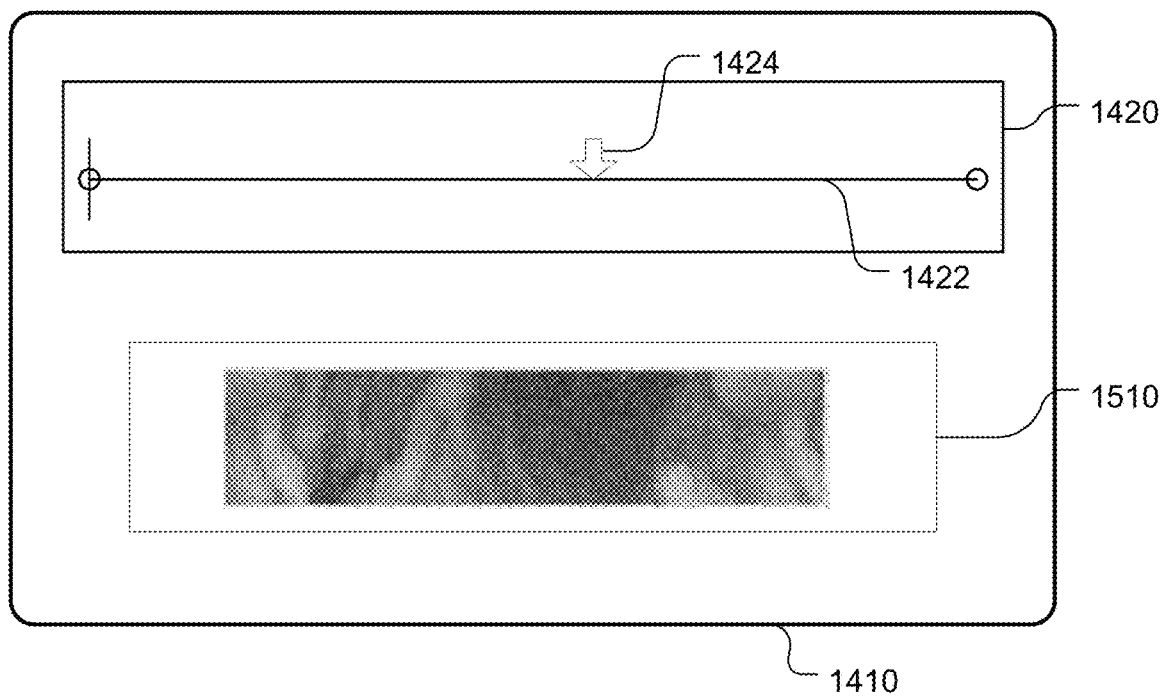
FIG. 15 illustrates another example of displaying the travelled distance information along with the image information similar to FIG. 14. However, the image as indicated by the marker is also shown in area on display instead of the time code.
Figure 16:
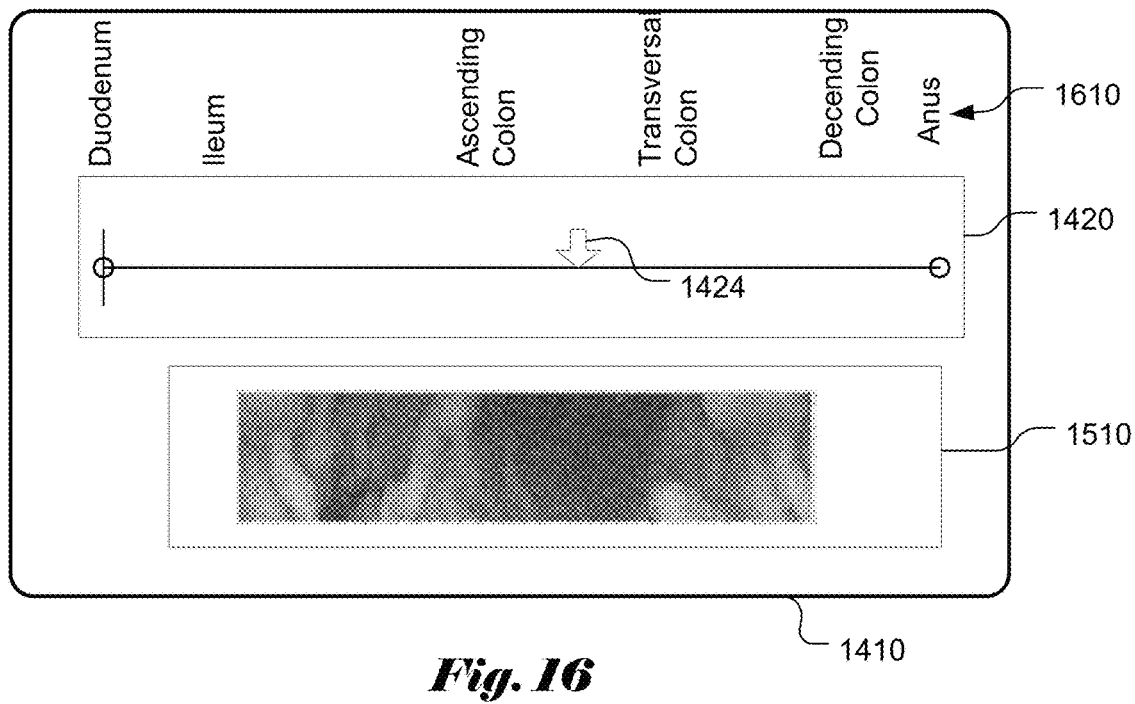
FIG. 16 illustrates yet another example of displaying the travelled distance information along with the image information, where the anatomic parts of the GI tract are also labelled across the graphic representation of the travelled distance.

The method may also display images or related information along with the travelled distance information on a display. FIG. 14 illustrates an example of displaying the travelled distance information along with the image information, where a graphic representation of the travelled distance 1420 and the time code of the image as indicated by a marker 1424 is shown in area 1430 on a display 1410. FIG. 15 illustrates another example of displaying the travelled distance information along with the image information, where the image as indicated by the marker 1424 is also shown in area 1510 on display 1410. FIG. 16 illustrates yet another example of displaying the travelled distance information along with the image information, where the anatomic parts 1610 of the GI tract are labelled across the graphic representation of the travelled distance. Similar to the case in FIG. 15, a user may pick a point in the travelled distance line (e.g. using a cursor displayed above the distance line) and the image corresponding to the location will be displayed in area 1510 on display 1410 in FIG. 16.

Figure 17:
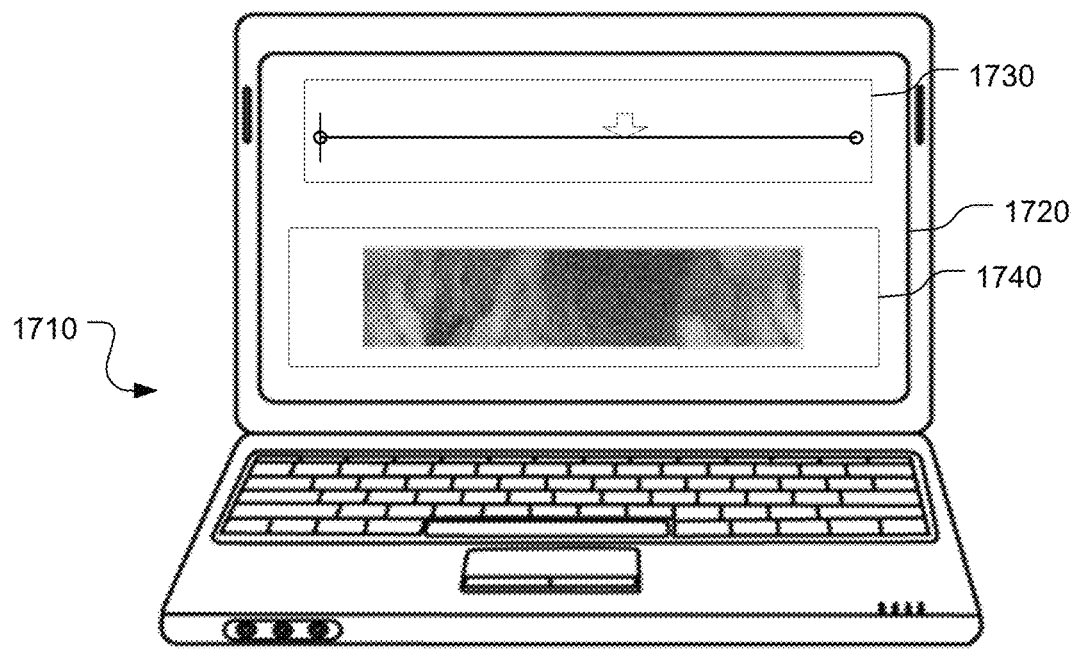
FIG. 17 illustrates an example of a notebook based implementation, where the CPU in the notebook will perform the needed processing and the travelled distance information and/or the corresponding image information can be displayed on the display (i.e., the notebook screen).

The method mentioned above can be implemented using various programmable devices such as micro-controller, central processing unit (CPU), field programmable gate array (FPGA), digital signal processor (DSP) or any programmable processor. A display can be used for presenting the visual information related to travelled distance and/or image information. Furthermore, mobile devices such as tablets or smart phones can be used to implement the method mentioned above since the mobile devices usually have a display and sufficient computational capability to handle the needed processing mentioned above. A notebook or a computer can also serve as the system to support the method mention above. For example, FIG. 17 illustrates an example of a notebook based implementation, where the CPU in the notebook 1710 will perform the needed processing and the travelled distance information 1730 and/or the corresponding image information 1740 can be displayed on the display 1720 (i.e., the notebook screen).

Figure 18:
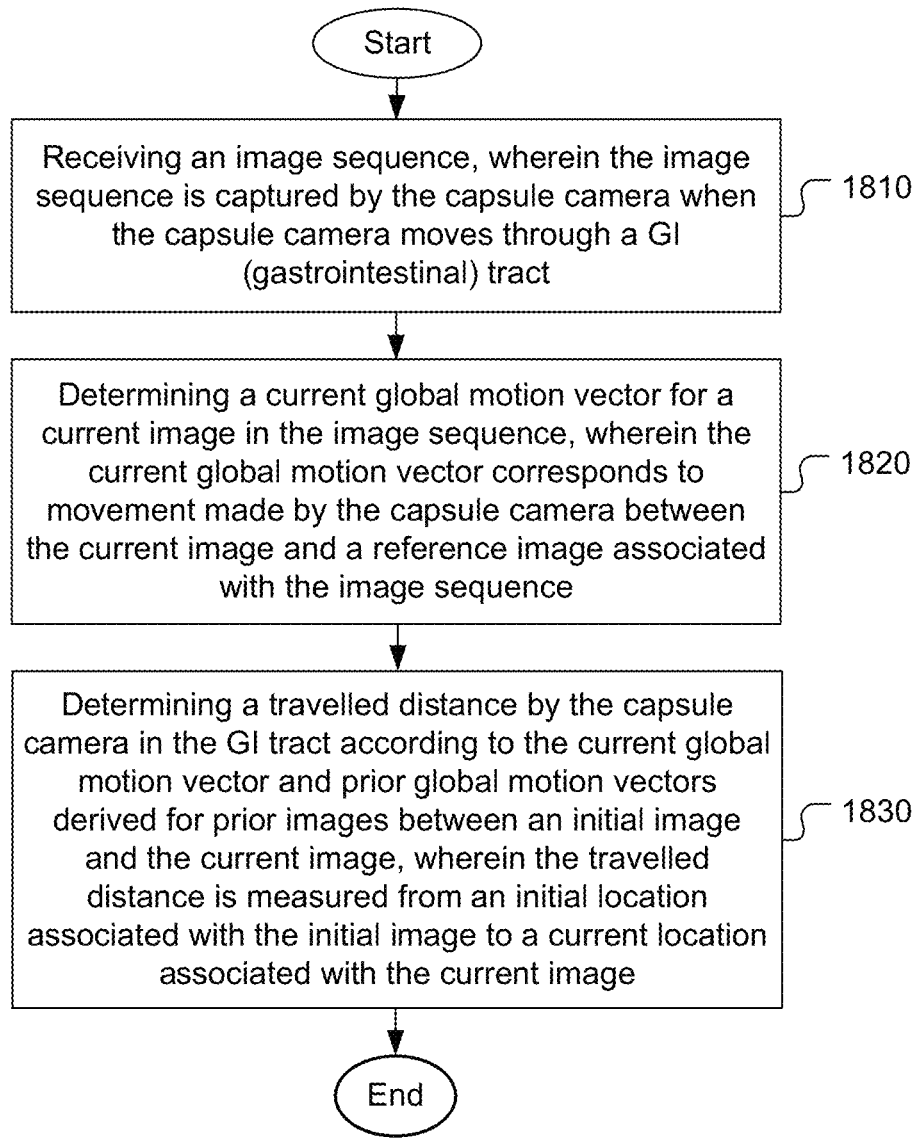
FIG. 18 illustrates an exemplary flowchart for determining a travelled distance by a capsule camera according to an embodiment of the present invention.

FIG. 18 illustrates an exemplary flowchart for determining a travelled distance by a capsule camera according to an embodiment of the present invention. According to this method, an image sequence is received in step 1810, where the image sequence is captured by the capsule camera when the capsule camera moves through a GI (gastrointestinal) tract. A current global motion vector for a current image in the image sequence is determined in step 1820, where the current global motion vector corresponds to movement made by the capsule camera between the current image and a reference image associated with the image sequence. A travelled distance by the capsule camera in the GI tract is determined according to the current global motion vector and prior global motion vectors derived for prior images between an initial image and the current image in step 1830, where the travelled distance is measured from an initial location associated with the initial image to a current location associated with the current image.

Figure 19:
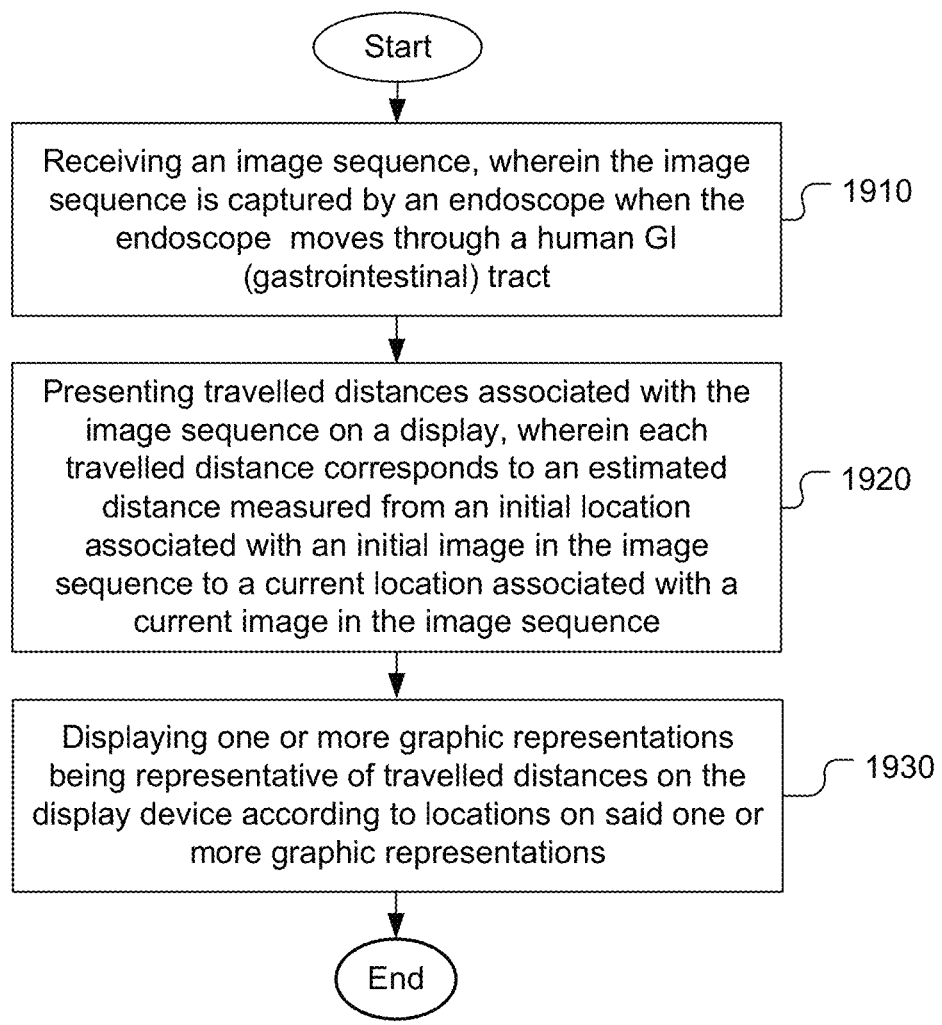
FIG. 19 illustrates an exemplary flowchart for displaying an image sequence captured by a capsule camera according to an embodiment of the present invention.

FIG. 19 illustrates an exemplary flowchart for displaying an image sequence captured by an endoscope according to an embodiment of the present invention. According to the method, an image sequence is received in step 1910, where the image sequence is captured by the endoscope when the endoscope travels through a human GI (gastrointestinal) tract. The travelled distances associated with the image sequence are presented on a display in step 1920, where each travelled distance corresponds to an estimated distance measured from an initial location associated with an initial image in the image sequence to a current location associated with a current image in the image sequence. One or more graphic representations being representative of travelled distances are displayed on the display device according to locations on said one or more graphic representations in step 1930.

The above description is presented to enable a person of ordinary skill in the art to practice the present invention as provided in the context of a particular application and its requirements. Various modifications to the described embodiments will be apparent to those with skill in the art, and the general principles defined herein may be applied to other embodiments. Therefore, the present invention is not intended to be limited to the particular embodiments shown and described, but is to be accorded the widest scope consistent with the principles and novel features herein disclosed. In the above detailed description, various specific details are illustrated in order to provide a thorough understanding of the present invention. Nevertheless, it will be understood by those skilled in the art that the present invention may be practiced.

The invention may be embodied in other specific forms without departing from its spirit or essential characteristics. The described examples are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A method of displaying an image sequence captured by an endoscope, the method comprising:
   receiving the image sequence, wherein the image sequence is captured by an endoscope camera of the endoscope when the endoscope travels through a human GI (gastrointestinal) tract;
   presenting, on a display device, travelled distances by the endoscope within the human GI tract, wherein the travelled distance is determined according to a current normalized global motion vector and prior normalized global motion vectors, wherein a current travelled distance corresponds to an estimated distance measured from the endoscope at an initial location associated with an initial image in the image sequence to the endoscope at a current location associated with a current image in the image sequence, wherein the current normalized global motion vector and the prior normalized global motion vectors are determined for the current image and previous images respectively, and wherein each normalized global motion vector is derived by normalizing a corresponding global motion vector associated with one image with respect to a nominal object distance between the endoscope camera and a GI tract wall; and
   displaying one or more graphic representations being representative of travelled distances by the endoscope on the display according to locations on said one or more graphic representations.

2. The method of claim 1, further comprising displaying an indicator on at least one of said one or more graphic representations to indicate a corresponding image associated with a target location pointed by the indicator.

3. The method of claim 2, further comprising displaying the corresponding image associated with the target location pointed by the indicator on the display.

4. The method of claim 1, further comprising indicating an anatomic part of the human GI tract at a target location on at least one of said one or more graphic representations, wherein corresponding images at the target location are associated with the anatomic part of the human GI tract.

5. A system for displaying an image sequence captured by an endoscope, the system comprising:
 a display device capable of displaying graphic information; and
 one or more electronic circuits or processors configured to:
  receive the image sequence, wherein the image sequence is captured by an endoscope camera of the endoscope when the endoscope travels through a human GI (gastrointestinal) tract;
  present, on a display device, travelled distances by the endoscope within the human GI tract, wherein the travelled distance is determined according to a current normalized global motion vector and prior normalized global motion vectors, wherein a current travelled distance corresponds to an estimated distance measured from the endoscope at an initial location associated with an initial image in the image sequence to the endoscope at a current location associated with a current image in the image sequence, wherein the current normalized global motion vector and the prior normalized global motion vectors are determined for the current image and previous images respectively, and wherein each normalized global motion vector is derived by normalizing a corresponding global motion vector associated with one image with respect a nominal object distance between the endoscope camera and a GI tract wall; and
 display one or more graphic representations being representative of travelled distances by the endoscope according to locations on said one or more graphic representations.

* * * * *